US005482842A

United States Patent [19]
Berndt

[11] Patent Number: 5,482,842
[45] Date of Patent: Jan. 9, 1996

[54] METHODS FOR DETECTING MICROORGANISMS IN BLOOD CULTURE VIALS

[75] Inventor: Klaus W. Berndt, Stewartstown, Pa.

[73] Assignee: Becton Dickinson and Company, Franklin Lakes, N.J.

[21] Appl. No.: 224,054

[22] Filed: Apr. 7, 1994

Related U.S. Application Data

[63] Continuation of Ser. No. 874,239, Apr. 24, 1992, abandoned.

[51] Int. Cl.$^6$ .............................. C12Q 1/04; C12M 1/34
[52] U.S. Cl. ............................ 435/34; 435/808; 250/345; 250/575
[58] Field of Search .................................. 435/29, 31, 34, 435/39, 287, 291, 296, 801, 807, 808; 472/82.05, 82.09, 83; 356/435, 436, 437; 250/575, 338.1, 340, 341, 343, 344, 345, 349, 341.1, 341.2, 341.7, 578.1

[56] References Cited

U.S. PATENT DOCUMENTS

| | | | |
|---|---|---|---|
| 3,975,727 | 8/1976 | Mader et al. | 356/435 |
| 4,017,193 | 4/1977 | Lotterman | 250/575 |
| 4,152,213 | 5/1979 | Ahnell | 195/103.5 M |
| 4,889,992 | 12/1989 | Hoberman | 250/343 |
| 4,945,060 | 7/1990 | Turner et al. | 435/291 |
| 4,971,900 | 11/1990 | Ahnell et al. | 435/29 |
| 5,155,019 | 10/1992 | Sussman et al. | 435/34 |

OTHER PUBLICATIONS

Thurman C. Thorpe, et al., "BacT/Alert: an Automated Colorimetric Microbial Detection System," *Journal of Clinical Microbiology*, Jul. 1990, pp. 1608–1612.
Rudolf F. Graf, "Modern Dictionary of Electronics," Howard W. Sams & Co., Inc., 5th Ed., 1982, p. 232.
Diagnostics Pasteur Brochure, Sixth International Congress on Rapid Methods and Automation in Microbiology and Immunology, Jun. 7–10, 1990, Helsinki, Finland.

*Primary Examiner*—William H. Beisner
*Attorney, Agent, or Firm*—Alan W. Fielder

[57] ABSTRACT

Methods and apparatus for detecting biological activity within a sample are disclosed. The present invention provides a combination of a first and a second infrared light source arranged on the side of a sample vial, and a first and a second narrow-band infrared detector similarly arranged on the side of the vial approximately opposite the sources. The disclosed arrangement cancels the sources of error while measuring the carbon dioxide content of the headspace gas above the sample. In operation, the present invention sequentially measures the photocurrents generated at each detector with no source turned on, with the first source turned on, and with the second source turned on and the first source turned off. The $CO_2$ absorption coefficient of the vial headspace gas is then calculated based on the photocurrents measured. This present invention allows compensation for source aging, detector aging, and vial wall thickness changes. Moreover, the present invention permits a determination of the absolute absorption coefficient at a selected wavelength, most preferably about 4.26 μm, which is the $CO_2$ absorption characteristic wavelength. The determination of the absolute $CO_2$ concentration within the headspace permits the detection of bacterial growth processes. Additionally, the disclosed source/detector combination can be produced at low cost. Thus, in preferred embodiments, the apparatus of the present invention comprises a plurality of vials that are simultaneously monitored by providing each of the plurality of vials with its own source/detector combination and activating and deactivating the sources and detectors using a multiplexer/demultiplexer arrangement.

8 Claims, 4 Drawing Sheets

METHODS FOR DETECTING MICROORGANISMS IN BLOOD CULTURE VIALS

This application is a continuation of application Ser. No. 07/874,239, filed Apr. 24, 1992, now abandoned.

The present invention relates to a non-invasive methods and apparatus for detecting biological activities in a specimen such as blood by measuring the absorption of light, and in particular to systems wherein the degree of absorption within the gaseous headspace above a specimen and a culture medium contained in a sealed container varies with the concentration of carbon dioxide generated by the metabolic processes of microorganisms.

BACKGROUND OF THE INVENTION

Usually, the presence of biologically active agents such as bacteria in a patient's body fluid, and especially in blood, is determined using blood culture vials. A small quantity of blood is injected through an enclosing rubber septum into a sterile vial containing a culture medium. The vial is typically incubated at 37° C. and monitored for bacterial growth.

Common visual inspection involves monitoring the turbidity or observing eventual color changes of the liquid suspension. Known instrumented methods detect changes in the carbon dioxide content of the culture bottles, which is a metabolic byproduct of the bacterial growth. Monitoring the carbon dioxide content can be accomplished by methods well established in the art, such as radiochemical (e.g., BACTEC®, Becton-Dickinson, Franklin Lakes, N.J., USA), infrared absorption at a carbon dioxide spectral line (e.g., NR-BACTEC®, Becton-Dickinson, Franklin Lakes, N.J., USA), or pressure/vacuum measurement such as those disclosed in U.S. Pat. No. 4,152,213—Ahnell. However, all these methods require invasive procedures which result in the well-known problem of cross-contamination within the vial. For purposes of this application, the term invasive implies that the confines of the sample container must be entered in order to determine if bacteria are present, e.g., a probe is inserted into a sealed vial. In the first two methods mentioned above, the headspace gas must be removed for analysis. In the case of vacuum/pressure measurement, while pressure is measured in a closed vial, any temperature change within the vial headspace also generates a pressure change that is not related to biological activity.

Therefore, an additional headspace temperature measurement is required in order to distinguish between biological and temperature-generated pressure effects. Non-invasive headspace temperature monitoring, however, represents a difficult problem, and no practical solutions are at hand. Additionally, some microorganisms can produce high pressure values while others produce relatively low or negligible ones. Thus, any pressure sensors used must be sensitive enough to allow detection of small changes in pressure while also being capable of safely measuring high pressure values. These two requirements are often mutually exclusive depending on the type of pressure sensor technology used. Thus far none of the pressure measurement systems known in the prior art permit the rapid and reliable detection of a wide variety of bacteria.

In order to circumvent the problems of cross-contamination, a non-invasive infrared microorganism detection instrument has been proposed in which special vials with infrared-transmitting windows are utilized. See U.S. Pat. No. 4,889,992—Hoberman. These vials, however, are relatively expensive. There is also an instrument in which glass vials are transferred to an infrared spectrometer by an automated manipulator arm and measured through the glass vial. This instrument is known as the BIO AGROS and is distributed by Diagnostics Pasteur, France. The disadvantage of this system is that, due to the high infrared absorption of glass, small changes in the glass wall thickness generate large errors in the measured headspace gas absorption. These problems can be partly reduced by utilizing high-quality glass vials, but this measure results in relatively high vial cost.

Recently, non-invasive methods have been developed involving chemical sensors disposed inside the vial. These sensors respond to changes in the carbon dioxide concentration by changing their color or by changing their fluorescence intensity. See, e.g., Thorpe, et al. "BacT/Alert: an Automated Colorimetric Microbial Detection System" J. Clin. Microb., July 1990, pp. 1608–12 and U.S. Pat. No. 4,945,060. These techniques are based on light intensity measurements and require spectral filtering in the excitation and/or emission signals. This means that errors can occur if any of the light source, the photodetector, the filters, or the sensor show aging effects over time which would vary the intensity response.

The disadvantage of such intensity-based methods can be overcome by utilizing a modulated excitation signal in combination with fluorescent sensors that change their fluorescent decay time with changing carbon dioxide concentration. In such a device, light intensity measurement is replaced with time measurement, and intensity changes and the related variations in sensor sensitivity therefore have no impact upon its operation. However, current fluorescent decay time sensors require high-brightness, short-wavelength light sources (550 nm or shorter) that are intensity-modulated at very high frequencies (typically about 100 MHz). Thus, for example, such a system might use a 5-mW green HeNe laser (543.5 nm), externally modulated by means of an acousto-optic light modulator, the operation of which is understood by those of ordinary skill. However, it will be realized that such a laser/modulator combination is rather expensive, requiring that the samples be moved to the laser, instead of having one light source at each sample. Such an instrument would therefore by necessity have a complicated mechanism for effecting the transportation of the individual samples to the light source and the time interval between successive measurements for each sample would be relatively long. It appears unlikely that high-brightness short-wavelength semiconductor diode lasers will be developed in the near future. Thus, even such an improved system would suffer serious practical shortcomings.

Thus, there remains an unmet need to provide a system for detecting microorganisms in samples that are sealed in vials that can tolerate the errors caused by the defects found in inexpensive glass vials. It is therefore an object of the present invention to overcome the limitations of the prior art described above by providing methods and apparatus for detecting biological activities in a specimen such as blood that are non-invasive and that do not require chemical sensors or any other additives within the specimen container. It is a further object of this invention to disclose a system that does not require high-brightness, short-wavelength light sources while also providing methods and apparatus that are safe against eventual extreme high pressure values while not being sensitive to headspace temperature changes. Another object of the present invention is to provide a system that is simple and inexpensive, so that each vial can be monitored continuously, thus allowing the construction of diagnostic instruments containing a plurality of stationary vials.

SUMMARY OF THE INVENTION

According to the present invention, the objectives set forth above are achieved by introducing a culture medium and a sample, such as a blood specimen, into a sealable glass vial and arranging a first and a second infrared light source on the side of the vial, positioned above the level of the liquid within the vial and at a fixed distance from each other. By then arranging a first and a second narrow-band infrared detector on the side of the vial approximately opposite the sources and also above the liquid level within the vial, the sources of error are cancelled. In operation, the present invention sequentially measures the photocurrents generated at each detector with no source turned on, with the first source turned on, and with the second source turned on and the first source turned off. The $CO_2$ absorption coefficient of the vial headspace gas is then calculated based on the photocurrents measured. This arrangement and measuring procedure allow compensation for source aging, detector aging, and vial wall thickness changes. Moreover, the present invention permits a determination of the absolute absorption coefficient at a selected wavelength, most preferably about 4.26 μm, which is the $CO_2$ absorption characteristic wavelength. The determination of the absolute $CO_2$ concentration within the headspace permits the detection of bacterial growth processes.

The present invention therefore provides methods of identifying the presence of biological activity within a sample contained in a vial that comprise the steps of disposing a first and a second source of infrared radiation at adjacent points on the vial and disposing a first and a second infrared detector at adjacent points on the vial that are substantially opposite from the first and second sources, respectively. Next, the first detector is activated to measure a background signal, $I_{CO}$, and then the first source is activated and an output signal, $I_{CA}$, is measured with the first detector. The first source is then deactivated and the second source activated to measure an output signal, $I_{CB}$, with the first detector. The first detector and the second source are deactivated and a background signal, $I_{DO}$, is measured with the second detector. The second detector is also used to measure an output signal from the first and second sources, $I_{DA}$ and $I_{DB}$. The methods of the present invention then proceed by calculating an absorption value from the background and output signals and repeating the steps of measuring the background and output signals from both the sources and both the detectors to determine further absorption values over time. The absorption values are then compared to determine if biological activity is present.

In preferred embodiments, the steps of activating and deactivating the sources and the detectors is carried out by a computer, as is the step of determining the absorption value. The step of determining the absorption value preferably comprises calculating the output signals for the first and second detectors as the first and second sources are activated and deactivated; and computing a value R according to the equation:

$$R = \frac{(I_{DB} - I_{DO})(I_{CA} - I_{CO})}{(I_{CB} - I_{CO})(I_{DA} - I_{DO})}$$

wherein $I_{CO}$ is the background signal of the first detector and $I_{DO}$ is the background signal of the second detector. The output signal of the first detector with the first source activated is $I_{CA}$ and with the second source activated is $I_{CB}$. Similarly, the output of the second detector is represented by $I_{DA}$ and $I_{DB}$ for the first and second sources, respectively.

In a most preferred embodiment, the methods of the present invention are carried out to identify the presence of biological activity for a plurality of samples. In such embodiments, the steps of activating and deactivating the first and second sources associated with each of the plurality of samples most preferably comprises transmitting an activation signal to a multiplexer and directing the activation signal to the first and second sources associated with one of the plurality of vials. Similarly, the activation and deactivation of the first and second detectors associated with each of the plurality of samples most preferably comprises the steps of receiving an output signal from a demultiplexer and creating a demultiplexer output signal associated with one of the plurality of vials.

In an apparatus made according to the present invention, the infrared sources are not modulated and no rotating filter wheel is required. The photocurrents are measured at a relatively low electronic detection bandwidth and preferably stored within a computer. The low detection bandwidth results in a high signal-to-noise ratio for the measured photocurrents. The function commonly accomplished by a mechanical chopper is taken over by the computer. The present invention therefore avoids any mechanically actuated sections. Additionally, the source/detector combination disclosed herein can be produced at low cost. Therefore, each vial preferably has its own source/detector combination, thereby allowing the construction of diagnostic instruments capable of monitoring a plurality of vials at the same time.

Apparatus for identifying the presence of biological activity within a sample contained in a vial made in accordance with the present invention therefore preferably comprises a first and a second source of infrared radiation disposed at adjacent points on the vial and a first and a second infrared detector disposed at adjacent points on the vial substantially opposite from the second and the first source respectively. A signal source selectively activates and deactivates the sources of infrared radiation. Preferably, a processor calculates an absorption value from an output signal received from at least each of the first and the second detector to permit the detection of biological activity if the absorption value measured is significantly higher than a absorption value measured at a previous point in time.

Preferably the apparatus of the present invention identifies the presence of biological activity in a plurality of samples. These embodiments include a first and second source of infrared radiation associated with each of the plurality of samples; and a signal source for transmitting an activation signal to a multiplexer for selectively directing the activation signal to the first and second sources associated with one of the plurality of samples. The apparatus also preferably comprises a first and second detector associated with each of the plurality of vials; and a demultiplexer for selectively receiving an output signal from the detectors associated with one of the plurality of vials and creating a demultiplexer output signal associated with one of the plurality of vials. In a most preferred embodiment of the apparatus of the present invention, the first and second sources of infrared radiation emit radiation at a wavelength of about 4.26 μm.

BRIEF DESCRIPTION OF THE DRAWINGS

FIG. 1 is a top view of a blood culture vial or similar sample container with two infrared sources disposed on one side of the vial and two infrared detectors on the other side.

FIGS. 2–4 are plots of the theoretical system output signal, R, versus the $CO_2$ absorption coefficient, $\mu_a$, for specific geometrical and spectral conditions for the device illustrated in FIG. 1.

DETAILED DESCRIPTION OF THE PREFERRED EMBODIMENTS

Figure 5:
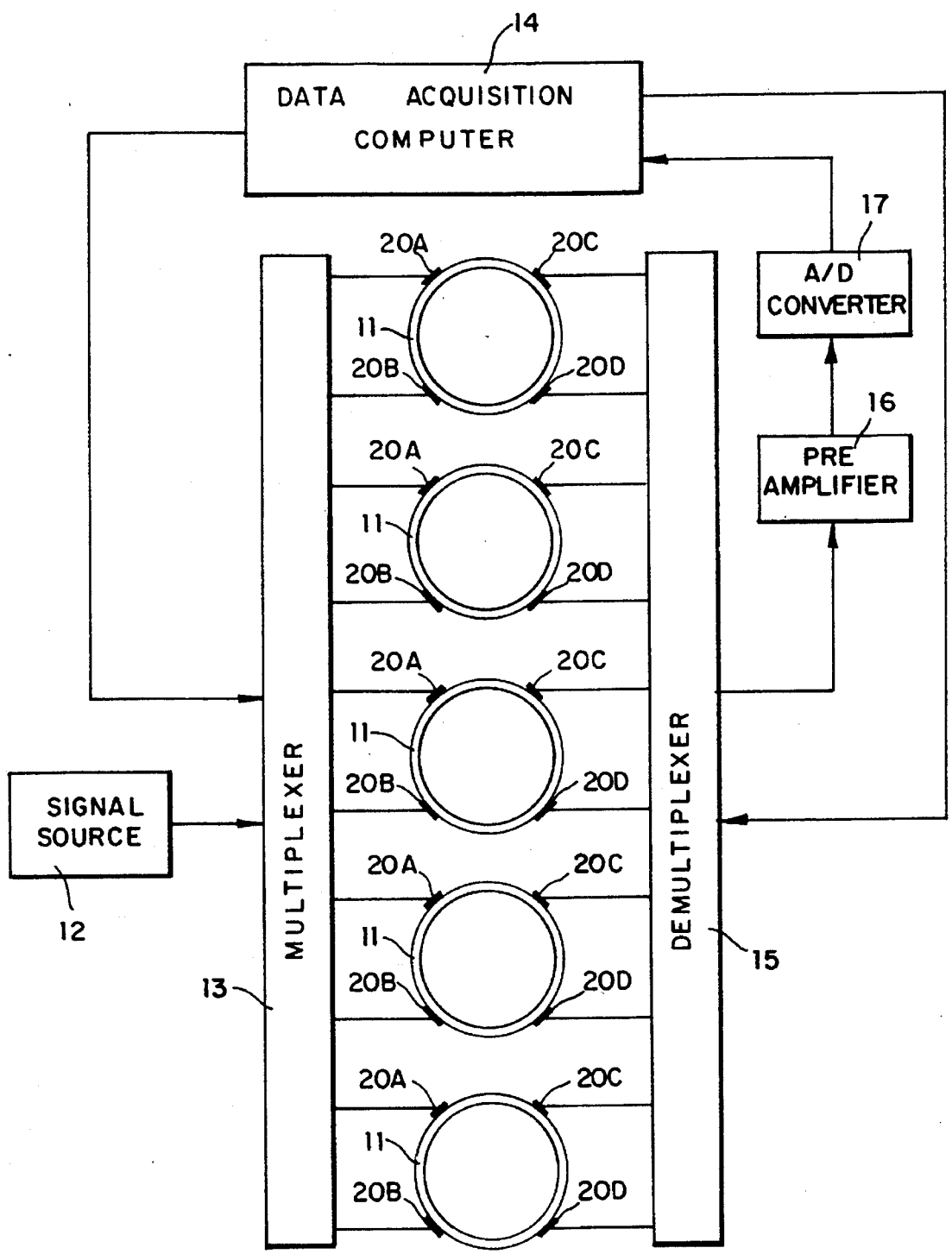
FIG. 5 is a schematic illustration of an apparatus for detecting microorganisms in a plurality of samples according to the present invention.

Referring now to FIG. 1 there is shown a top view of a blood culture vial 11 with a first infrared source 20A and a second infrared source 20B disposed on one side of the vial, and a first 4.26 μm narrow-band infrared detector 20C and a second 4.26 μm narrow-band infrared detector 20D disposed at two points on the other side. In this particular case, the first infrared source 20A and the second detector 20D are arranged opposite to each other, as are the second infrared source 20B and first detector 20C. In a preferred embodiment, the angle between the lines connecting the first source 20A with the second detector 20D, and the second source 20B with the first detector 20C is between about 20° and about 90°. This arrangement of sources and detectors results in equal optical headspace gas path lengths, i.e., $L_1=AC=BD$ and $L_2=AD=BC$, respectively, as shown in FIG. 1. In order to obtain the best results, each source/detector pair should be diametrically opposed, i.e., $L_1$ in FIG. 1 should pass through the geometric center of the vial 11. In general, however, apparatus made according to the present invention is not restricted to the geometrical arrangement depicted in FIG. 1. Additionally, the sources 20A, 20B and detectors 20C, 20D can be arranged at different heights above the liquid level in order to establish path length differences between the straight lines AD and AC as well as between BC and BD if desired. Most preferably, the infrared sources 20A, 20B and detectors 20C, 20D emit and receive infrared radiation at a wavelength of about 4.26 μm, the characteristic wavelength of carbon dioxide.

Methods for measuring the absorption coefficient according to the present invention preferably comprise a first step of detecting a background signal when no infrared source is turned on. The background signal, $I_{CO}$, of the detector 20C is measured and background signal, $I_{DO}$, of the detector 20D is also measured. Next, the first infrared source 20A is turned on, and the signal, $I_{CA}$, of detector 20C is measured. This signal can be described in the form:

$$I_{CA}=I_A R_C F\ e^{-a'\mu G}\ e^{-c'\mu G}[\ (1-k)+ke^{-L1\ \mu a}]+I_{CO} \qquad (1)$$

In equation (1), $I_A$ is the infrared power emitted by the first infrared source 20A, $R_C$ is the responsivity of first detector 20C, and F is a general geometry factor taking into account such properties as source emission divergence and detector aperture. The quantity k characterizes the spectral fraction of radiation absorbed by $CO_2$ molecules relative to the spectral window of the infrared detector. The glass absorption is represented by $\mu_g$, and the $CO_2$ absorption coefficient is $\mu_a$.

The thickness of the vial wall at the first source 20A is denominated by a, and the thickness at the first detector 20C by c. The quantities a' and c' in equation (1) are different from a and c, because the first source 20A and the first detector 20C are not arranged exactly opposite one another, as shown by line $L_1$ in FIG. 1. For a distance, s, between the first and second sources 20A, 20B and a vial diameter, v, the angle $\alpha=ACB$ (i.e., the angle formed by $L_1$ and $L_2$ in FIG. 1) can be obtained using the expression: $\sin \alpha=s/v$. Within the glass wall, $\alpha$ is replaced by $\beta$, with $n(\sin \beta)=\sin \alpha$, and $n=1.5$ being the refractive index of glass. From FIG. 1, the expressions $a'=a/\cos \beta$ and $c'=c/\cos \beta$, respectively, are derived.

The radiation emitted by the first source 20A is then measured with the second detector 20D. The output signal of this detector 20D is:

$$I_{DA}=I_A R_D F\ e^{-a\mu G}e^{-d\mu G}[\ (1-k)+ke^{-L2\mu a}]+I_{DO} \qquad (2)$$

Next, the first source 20A is turned off, source 20B is turned on, and the signal, $I_{CB}$, of the first detector 20C is measured. This signal can be described in the form:

$$I_{CB}=I_B R_C F\ e^{-b\mu G}e^{-c\mu G}[(1-k)+ ke^{-L2\mu a}]+I_{CO} \qquad (3)$$

In equation (3), $I_B$ is the infrared power emitted by the second source 20B. The next step comprises measuring the radiation emitted by the second source 20B with the second detector 20D. The output signal of this detector is:

$$I_{DB}=I_B R_D F\ e^{-b'\mu G}e^{-d'\mu G}[(1-k)+ ke^{-L1\mu a}]+I_{DO} \qquad (4)$$

In equation (4) the effective glass path lengths b' and d' are: $b'=b/\cos \beta$ and $d'=d/\cos\beta$, respectively, with b and d being the respective wall thicknesses at the second source 20B and the second detector 20D.

All these output signals from the detectors 20C, 20D are preferably stored within the memory of a computer. When all the signals have been measured, the computer calculates the quantity, $R(\mu_a)$, with:

$$R=\frac{(I_{DB}-I_{DO})(I_{CA}-I_{CO})}{(I_{CB}-I_{CO})(I_{DA}-I_{DO})} \qquad (5)$$

Using equations (1) to (5), the expression:

$$R(\mu_a) = e^{-q(a+b+c+d)\mu G}\left[\frac{(1-k)+ke^{-L1\mu_a}}{(1-k)+ke^{-L2\mu_a}}\right]^2 \qquad (6)$$

is obtained for the $CO_2$ concentration dependent system output signal, $R(\mu_a)$. Equation (6) shows that the power of the infrared sources $I_A$ and $I_B$, the geometry factor F, and the responsivities of the detectors $R_C$ and $R_D$ are cancelled out using the arrangement of sources and detectors described above with reference to FIG. 1. Therefore, the present invention provides a system that does not show any aging drifts related to the sources 20A, 20B or detectors 20C, 20D.

One of ordinary skill in the art will realize that in an apparatus according to the present invention, the infrared sources are not modulated, and no rotating filter wheel is required. In the prior art, the apparatus response function had been eliminated by comparing an absorption measurement performed at a $CO_2$ spectral line with an absorption measurement performed at a wavelength close to a $CO_2$ spectral line. Therefore, apparatus such as a rotating filter wheel was commonly used to create signals of two different wavelengths. It is impractical, however, to arrange one filter wheel at each vial or sample container in a device for simultaneously testing hundreds of vials. Alternatively, if one infrared source and two detectors having a different spectral window were used, the glass wall changes near the two detectors would not be canceled out. However, in the preferred embodiments of an apparatus constructed according to the present invention, these variations are canceled out to a high degree, as will be shown below.

Additionally, in the present invention, the photocurrents are measured at a relatively low electronic detection bandwidth and are preferably stored within a computer. The low detection bandwidth results in a high signal-to-noise ratio for the measured photocurrents. The function of detector background signal discrimination, accomplished in the prior art by a mechanical chopper, is taken over by the computer. This principle avoids any mechanically moving parts and the source/detector combination described above and shown in FIG. 1 can be produced at low cost, permitting each vial 11 to have its own source/detector combination and allowing the construction of diagnostic instruments capable of processing hundreds of non-moving vials.

In equation (6) set forth above, the quantity q is equal to $(1/\cos \beta) - 1$. For $\beta$ values up to about 20°, i.e., for a-values up to about 30°, q can be approximated by $(\frac{1}{2})(s/nv)^2$ and the relation $q \leq 0.05$ is valid. As an example, $q=0.05$ for $\alpha=27°$, and $q=0.02$ for $\alpha=18°$. This means that changes in the vial wall thickness have a much smaller effect as compared to a standard detector. In other words, a typical low-cost vial with a wall thickness variation of ±0.5 mm is transformed into a high-quality vial with an effective wall thickness variation of ±25 μm —an improvement by a factor of 20.

The operation and advantages of apparatus made according to the present invention can be illustrated more clearly by calculating the relative error in the system output signal, $R(\mu_a)$, caused by a variation in the wall thickness of the sample vial. For a device with only one source and one detector, equation (2) is used to obtain the relation:

$$\frac{dI_{DA}/I_{DA}}{da} = -\mu_G \quad (7)$$

For an apparatus according to the present invention, equation (7) is used to obtain the relation:

$$\frac{dR/R}{da} = -q\mu_G \quad (8)$$

Comparison of equations (7) and (8) shows that the relative error in an apparatus according to the present invention is reduced significantly because $q \ll 1$. In equation (2), two glass wall contributions are effective. In equation (7) this number is doubled. In practice, however, a partial cancellation of the four variations can be expected because the glass wall variations are likely to be a mixture of positive and negative ones.

As mentioned above, the quantity k in equation (6) characterizes the spectral fraction of radiation absorbed by $CO_2$ molecules, relative to the spectral window of the infrared detectors 20C, 20D. In an apparatus according to the present invention, a high k-value is preferred, most preferably as close to 1 as possible. The rationale for this preference can be seen by comparing FIGS. 2–4, where theoretical plots of $R(\mu_a)$ are shown for different geometrical and spectral conditions. These plots are normalized to $R=1$ for $\mu_a=0$.

FIG. 2 shows R versus $\mu_a$ for a vial with an inner diameter v=39 mm (e.g., a standard BACTEC® vial supplied by Becton Dickinson Diagnostic Instrument Systems, Sparks, Md.), and with a distance s=19 mm between infrared sources 20A and 20B ($\alpha=29°$). For these plots, high k-values between 0.80 and 0.95 are assumed. High k-values can be obtained by utilizing extreme narrow-band infrared detectors. As well known to those of ordinary skill, a narrow-band detector can be realized by means of a narrow-band filter combined with a broad-band detector.

Figure 3:
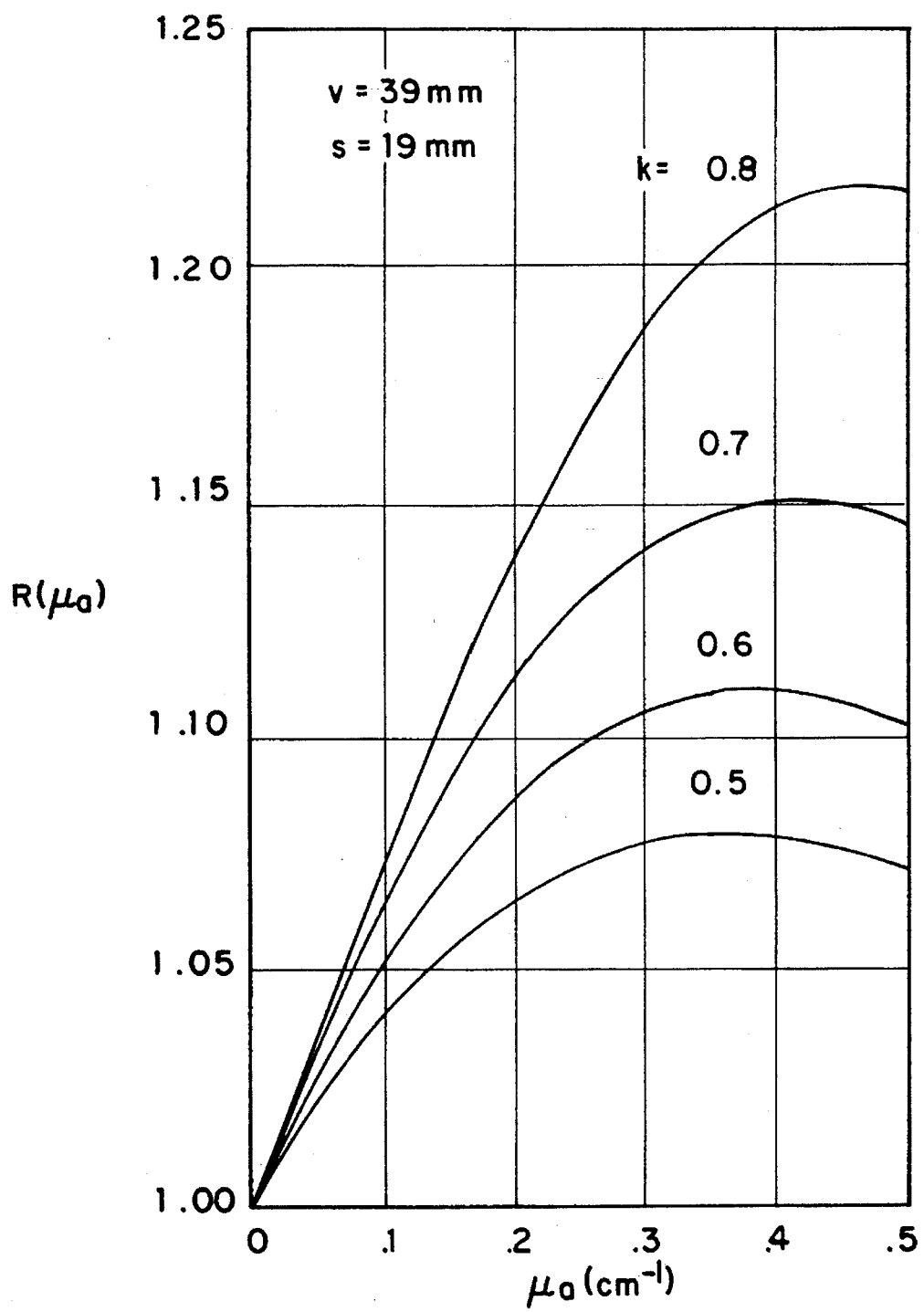

FIG. 3 shows a plot of $R(\mu_a)$ under conditions similar to those in FIG. 2, but assuming lower k-values, between 0.5 and 0.8. The lower k-values result from usage of infrared detectors 20C, 20D that are less wavelength-selective. Comparison of FIG. 3 with FIG. 2 shows that lower k-values require more sophisticated electronic detection devices because the sensitivity is reduced. In other words, improvements in k-values increase the sensitivity of the present invention.

Figure 4:
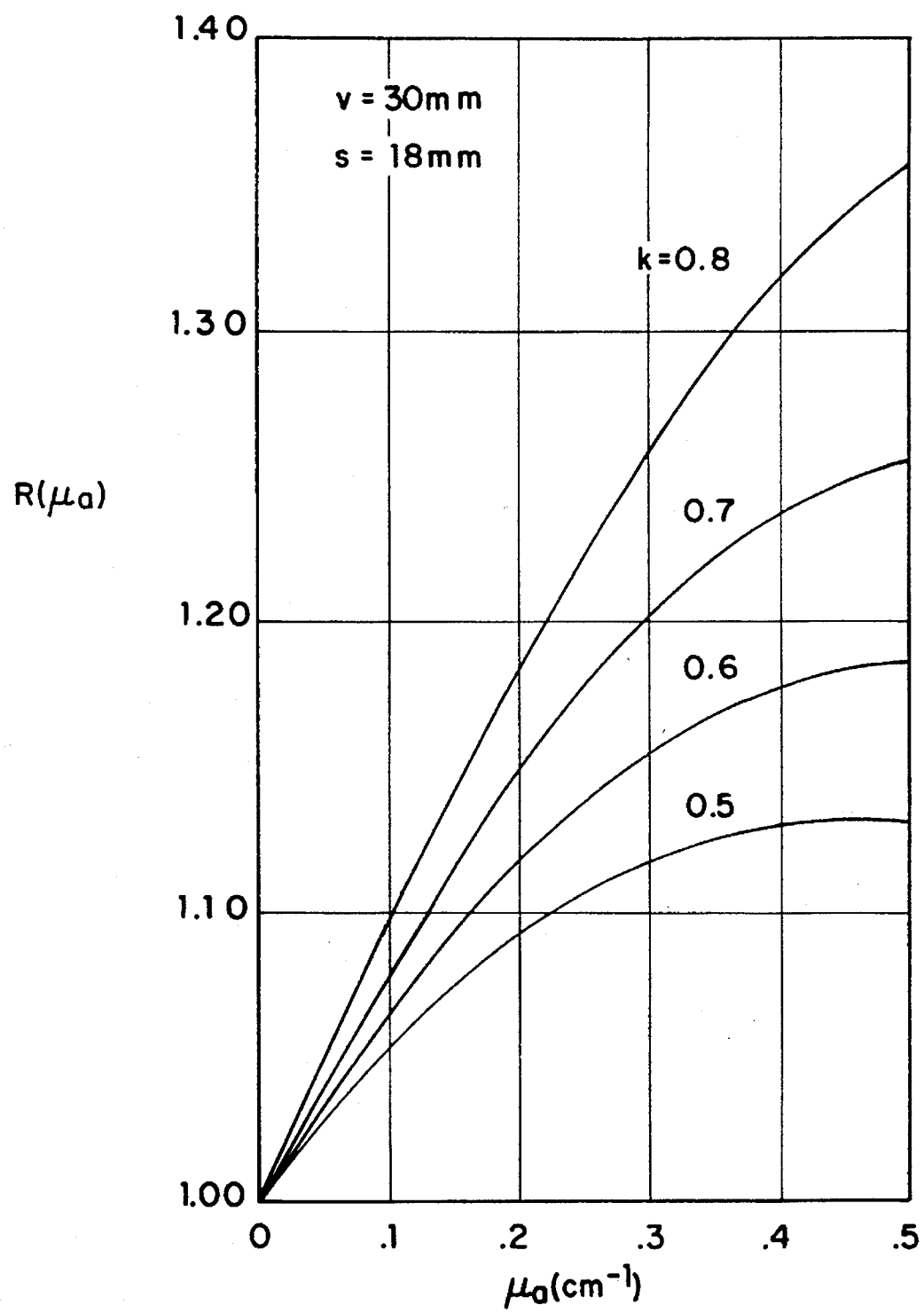
Figure 5:
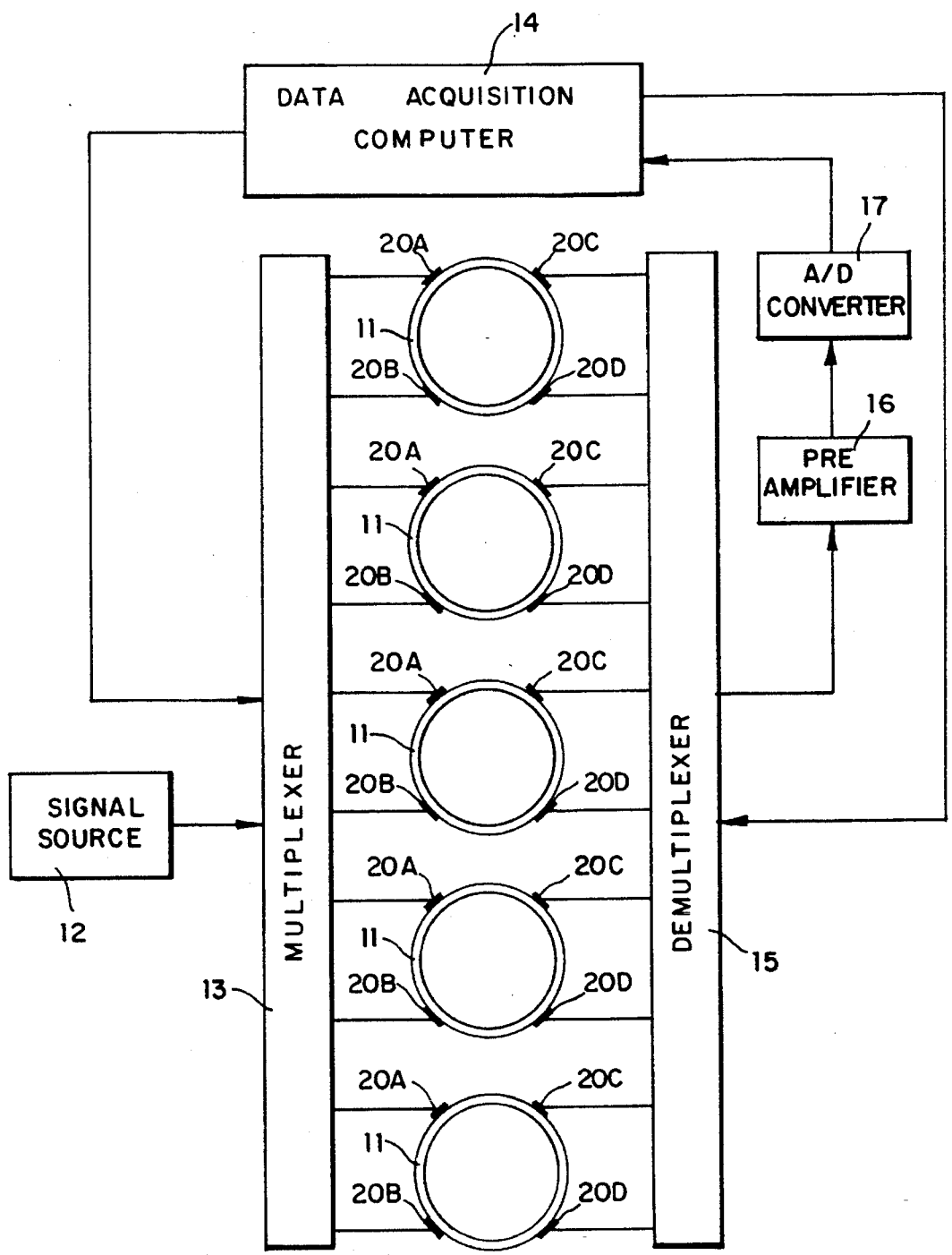

FIG. 4 shows a plot of R versus $\mu_a$ for a vial with a smaller inner diameter than the vial for which the data in FIGS. 2–3 were derived. The vial used in FIG. 4 has an inner diameter v=30 mm, and a distance s=18 mm between infrared sources 20A and 20B. For these plots, lower k-values between 0.5 and 0.8 have been assumed. As can be seen by comparing FIG. 4 with FIG. 3, reduced vial diameters result in an increased sensitivity, and in an increased dynamic range for $\mu_a$.

The arrangement and measuring procedures described above allow for the compensation of source aging, detector aging, and vial-to-vial wall thickness variations. If a typical vial wall thickness a=b=c=d=2.5 mm is assumed, along with a glass absorption coefficient $\mu_a=5$ cm$^{-1}$ and q=0.02, then the pre-factor $\exp[-q(a+b+c+d)\mu_g]$ in equation (6) becomes about 0.9. If it is also assumed, as a worst case scenario, that all wall thicknesses, a, b, c, and d, have the same vial-to-vial variation (amount and sign) of ±0.5 mm, then for the relative variation in the system output signal, dR/R, a value of ±2% is obtained. This means that an apparatus according to the present invention permits the determination of the absolute value of $\mu_a$ within the vial headspace. Therefore, a determination of the absolute $CO_2$ concentration within the headspace is possible if the filter-related k-factor is known. In other words, despite using low-cost vials, a threshold for R can be set in order to distinguish positive vials exhibiting biological activity from negative ones. Finally, it should be noted that for a single vial the vial-to-vial variations —da, db, dc, and dd have little or no impact on the time course of R(t). Taking into consideration the total source intensity and detector responsivity compensation, small changes in the $CO_2$ concentration will therefore be detectable.

A preferred embodiment of a detection apparatus for monitoring a plurality of vials that embodies the principles and concepts of the present invention described above is depicted schematically in FIG. 5. The apparatus is preferably comprised of a plurality of sealed glass vials 11 inoculated with a medium/blood mixture, i.e., typical blood culture vials. As discussed above with reference to FIG. 1, first and second infrared sources 20A, 20B are arranged on one side of each vial above the liquid level, and first and second narrow-band infrared detectors 20C, 20D are arranged on the other side of each vial above the liquid level. The apparatus made according to the present invention further comprises a DC power supply 12 which is connected to the input of a multiplexer 13 which is controlled by a computer 14 to selectively activate the sources and detectors in the manner described above, as well as to sequentially cause such activation to occur vial-to-vial. The output channels of the multiplexer 13 are connected to the first and second infrared sources 20A, 20B located adjacent each vial 11 and the electrical signal provided by the multiplexer activates the sources 20A, 20B. The outputs of all the infrared detectors 20C, 20D are connected to the inputs of a demultiplexer 15 which is also preferably controlled by the computer 14. The demultiplexer 15 functions to coordinate the signals received from the plurality of detector pairs so that the data associated with each vial can be identified. The analog output signal of the demultiplexer 15 is fed to the input of a preamplifier 16 and the amplified output signal is preferably digitized by an analog-to-digital converter 17. The digital output signal of the analog-to-digital converter 17 is preferably stored in the computer 14 for processing as described above.

In operation, the computer-controlled multiplexer 13 sequentially carries out the steps described above with reference to FIG. 1 on each vial 11 by alternately activating and deactivating the first source 20A and second source 20B. The demultiplexer 15 ensures that the data that are related to the individual vials are kept separated and identified when output and stored. The system cycles through each vial 11 in the instrument and then begins the process again. As noted above, the presence of bacterial growth will cause a marked increase in the concentration of $CO_2$ in the headspace gas above the blood/culture sample disposed within each vial 11. The data collected by the system depicted in FIG. 5 can therefore be used by either transmitting these data to an operator or by programming the computer 14 to identify those vials 11 exhibiting increased $CO_2$ concentration.

Although certain embodiments of the present invention have been set forth with particularity, these embodiments are for the purposes of illustrating the present invention and are not meant to be limiting. As will be readily understood by those of ordinary skill numerous variations, modifications and adaptations of the concepts disclosed herein are possible. For example, the samples are not limited to blood/culture samples, nor are the detectors meant to be limited to the detection of $CO_2$ concentration alone. As discussed above, the geometry of the sources and detectors can be varied while still achieving useful results. Therefore, in order to determine the full scope of the present invention, reference should be made to the appended claims.

What is claimed is:

1. A method of identifying the presence of biological activity within a sample contained in a vial by measuring absorption of infrared radiation by a gas in a head space over the sample within the vial, said method comprising the steps of:

disposing a first and a second source of infrared radiation on a wall of a vial adjacent to a head space over a sample within the vial;

disposing a first and a second infrared detector on the wall of the vial adjacent to the head space within the vial and substantially opposite from the first and second source, respectively, so that infrared radiation from each source passes through the wall of the vial and the head space to both detectors;

activating the first detector to measure a first background signal ($I_{CO}$);

activating the first source and measuring a first output signal ($I_{CA}$) with the first detector;

deactivating the first source, activating the second source and measuring a second output signal ($I_{CB}$) with the first detector;

deactivating the first detector and the second source, and activating the second detector to measure a second background signal ($I_{DO}$);

activating the first source and measuring a third output signal ($I_{DA}$) with the second detector;

deactivating the first source, activating the second source and measuring a fourth output signal ($I_{DB}$) with the second detector;

calculating a first absorption value R(1) as follows:

$$R(1) = \frac{(I_{DB} - I_{DO})(I_{CA} - I_{CO})}{(I_{CB} - I_{CO})(I_{DA} - I_{DO})} \;;$$

repeating the activating and deactivating steps;

calculating a second absorption value R(2) as follows:

$$R(2) = \frac{(I_{DB} - I_{DO})(I_{CA} - I_{CO})}{(I_{CB} - I_{CO})(I_{DA} - I_{DO})} \;; \text{and}$$

comparing the absorption values R(1) and R(2) to determine if biological activity is present in the sample in the vial, as evidenced by the second absorption value R(2) being greater than the first absorption value R(1).

2. The method of claim 1 wherein the steps of activating and deactivating the sources and the detectors is carried out by a computer.

3. The method of claim 1, wherein the steps of calculating the first and second absorption values is carried out by a computer.

4. The method of claim 1, further comprising providing a plurality of said vials, each containing said sample, such that the absorption values R(1) and R(2) are calculated for each of said vials so as to determine if biological activity is present in the sample in the vial.

5. The method of claim 4, further comprising providing a plurality of first and second sources, with each first and second source being associated with one of the plurality of said vials, and wherein the steps of activating and deactivating the first and second sources associated with each one of the plurality of said vials comprises the steps of transmitting an activation signal to a multiplexer and directing the activation signal to the first and second sources associated with said one of the plurality of said vials.

6. The method of claim 4, further comprising providing a plurality of first and second detectors, with each first and second detector being associated with one of the plurality of said vials, and wherein the steps of activating and deactivating the first and second detectors associated with each one of the plurality of said vials comprises the steps of receiving an output signal from a demultiplexer and creating a demultiplexer output signal associated with said one of the plurality of said vials.

7. The method of claim 6, further comprising the step of amplifying the demultiplexer output signal.

8. The method of claim 6, further comprising the step of converting the demultiplexer output signal into digital form.

* * * * *